United States Patent [19]

Tada et al.

[11] 4,182,036
[45] Jan. 8, 1980

[54] ORTHODONTIC UNIT DISPOSITION STRUCTURE

[75] Inventors: Yasuyuki Tada, Takatsuki; Yutaka Ohta, Kyoto, both of Japan

[73] Assignee: Kabushiki Kaisha Morita Seisakusho, Kyoto, Japan

[21] Appl. No.: 882,196

[22] Filed: Feb. 28, 1978

[30] Foreign Application Priority Data

Feb. 28, 1977 [JP] Japan .................. 52/021868

[51] Int. Cl.$^2$ ............................................. A61C 19/02
[52] U.S. Cl. ........................................ 433/2; 433/33
[58] Field of Search ..................... 32/1, 22, DIG. 9

[56] References Cited

U.S. PATENT DOCUMENTS

| | | | |
|---|---|---|---|
| 3,497,955 | 3/1970 | Gallagher | 32/22 |
| 3,757,420 | 9/1973 | Silverman | 32/22 |
| 3,922,788 | 12/1975 | Rota | 32/22 |
| 4,095,379 | 6/1978 | Weintraub | 32/22 |

OTHER PUBLICATIONS

The Weber Dental Manufacturing Co., Canton, Ohio, 44705, Weber Dental Catalogue, Design #2, p. 14, plan No. 9878-1-B, May 1969.
Dentsply Equipment, Dentsply International, York, Penna., p. 1.

*Primary Examiner*—Robert Peshock
*Attorney, Agent, or Firm*—Koda and Androlia

[57] ABSTRACT

This invention discloses an orthodontic unit disposition structure wherein a clinical area and a consultation area are provided in an adjacent relation with each other so as to carry out systematic and rational treatment and instruction from first to last whereby a patient can have his case initially diagnosed and then receive treatment and instruction, thus being enabled to undergo an effective operation.

2 Claims, 4 Drawing Figures

ORTHODONTIC UNIT DISPOSITION STRUCTURE

BACKGROUND OF THE INVENTION

1. Field of the Invention

This invention relates to an orthodontic unit disposition structure in orthodontics, and more particularly to an orthodontic unit disposition structure in orthodontics in which structure a dentist is capable of carrying out an initial diagnosis and then treatment and instruction of patients systematically and rationally from first to last.

2. Prior Art

As well know, orthodontics is considered dental speciality in provision of normal occlusion by correcting abnormally aligned or positioned teeth. This correction treatment, however, does not end in a short time but is generally carried out over a considerably long period of time under a close program of treatment. In carrying out the treatment, it becomes necessary that an operator and a patient, or the operator, patient and his parent should consult and cooperate with each other, because it is more often the case with children in their stage of growth that receive orthodontic treatment. Also orthodontic treatment is special treatment different from ordinary dental treatment. The former is different from the latter in treatment instrument, material and the posture which a patient takes, the position which an operator takes with respect to the patient, and the like, with the result that it is necessary to provide an environment suited for exclusive use in orthodontics. Also, the patient has to receive instruction from the operator or his assistant (a nurse) as to what the patient himself has to do every day, such as how to set a rubber ring and how to control the band of chin cap. In this manner, it is necessary that the operator and patient, or the operator, his assistant, patient and his parent should cooperate with one another in treatment and that the operator should take the most rational posture toward the patient to carry out quick treatment and work without giving pain to the patient.

But in reality there were no such environment and equipment for exclusive use in orthodontics as could meet the requirements described above, since heretofore it was a general practice for the operator to manage to use in the field of orthodontics the instruments, materials and cabinets, etc., fit for use in general dental treatment. For this reason, only irrational and inefficient treatment was available to the patient, thereby causing a delay in treatment.

SUMMARY OF THE INVENTION

In view of the problems described above, it is a primary object to provide a treatment unit disposition structure which is exclusively used in orthodontics and which can satisfy all the demands stated above.

That is to say, when a patient comes to a doctor's office, the operator makes a first medical examination of the patient and works out a treatment program on the basis of the examination and enters into a practical orthodontic treatment action inclusive of instruction for the patient, and this invention is intended to make it possible for the operator to effectively continue a series of his actions more conveniently from first to last.

The object described above can be attained by arranging a clinical area and a consultation area next to each other and permitting free communication between the two areas. Namely, in the clinical area, organization of treatment work around the patient on the treatment table by the operator and his assistant is easily effected, while in the consultation area an exchange of questions and answers between the oeprator and the patient (including his or her parent), diagnosis, observation, instruction, etc., of the patient are systematically carried out. A preferred embodiment of the invention will now be described by way of example only with reference to the accompanying drawings.

DESCRIPTION OF THE PREFERRED EMBODIMENT

Figure 1:
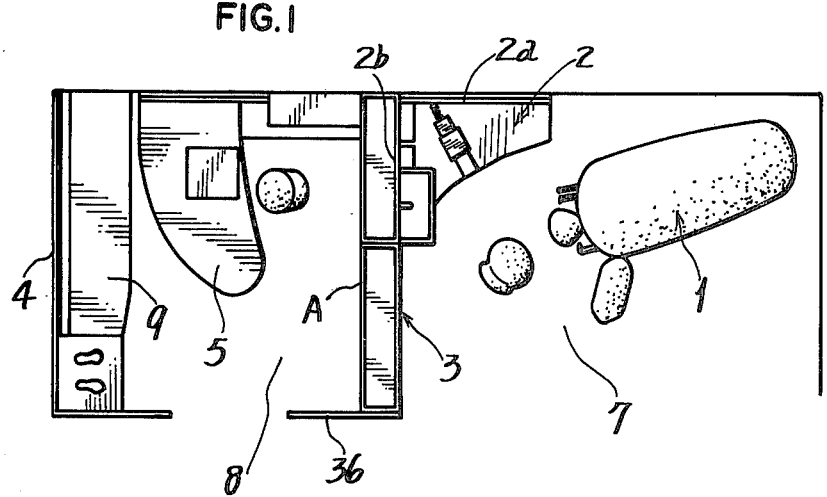
FIG. 1 is a plan view of a preferred embodiment of this invention.
Figure 2:
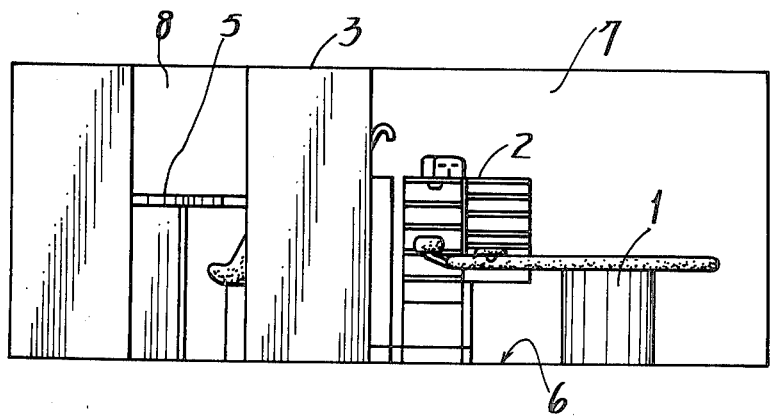
FIG. 2 is a front view of the same in FIG. 1.
Figure 3:
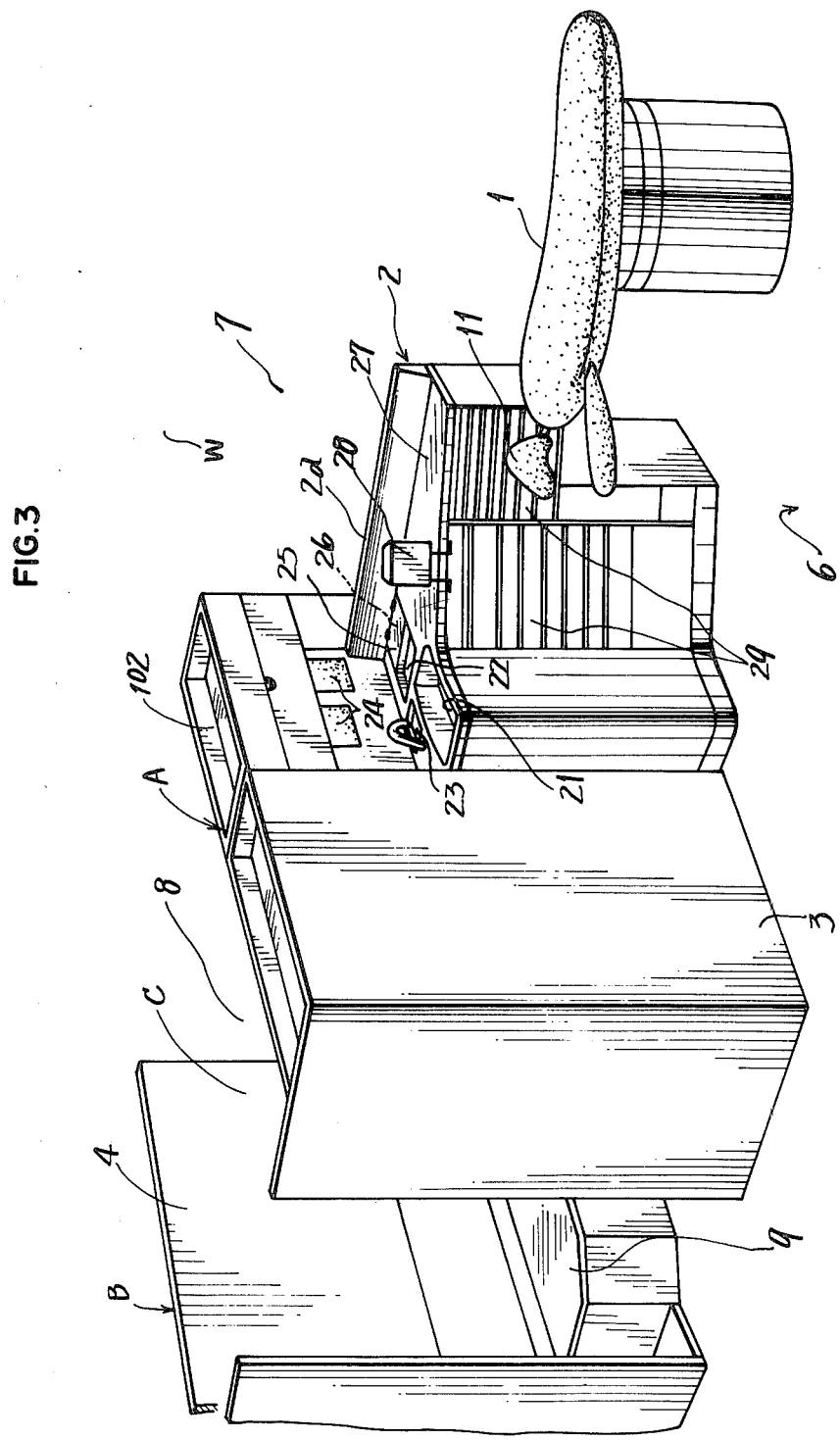
FIG. 3 is a perspective view showing the state of arrangement of a cabinet and treatment table.
Figure 4:
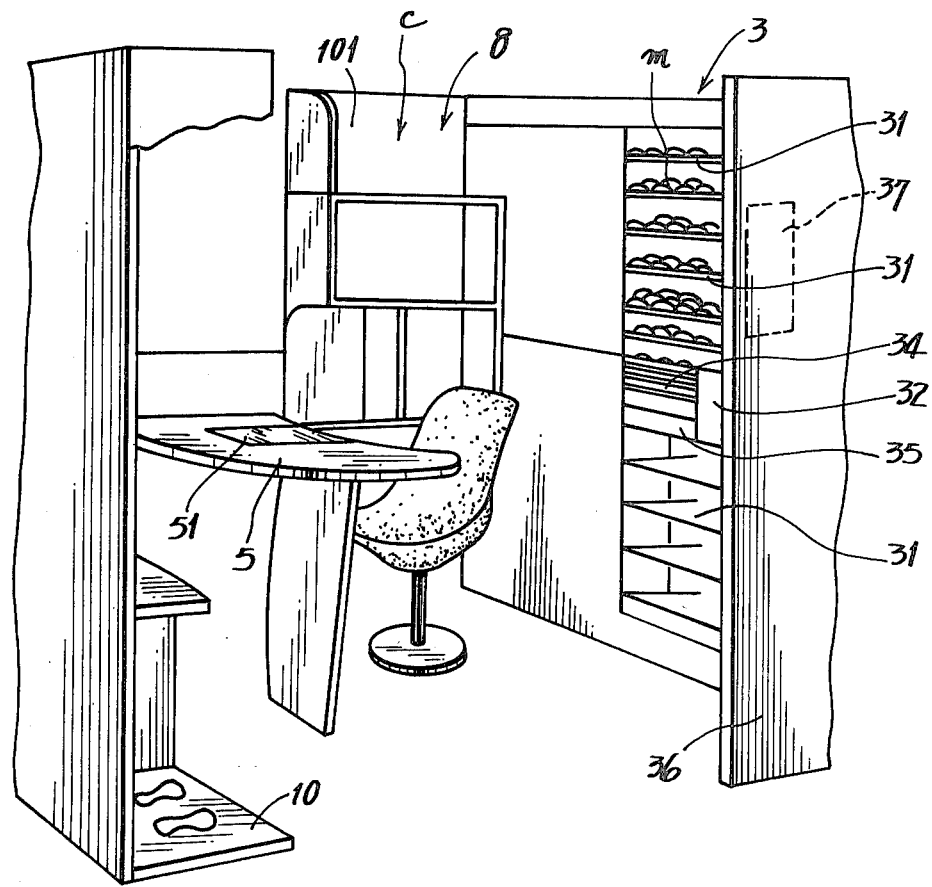
FIG. 4 is a perspective view of a consultation area.

FIGS. 1 through 4 show a preferred embodiment of an orthodontic unit disposition structure according to this invention in a plan, a front and a perspective view respectively. In the drawings, numeral 7 designates a clinical area. The clinical area 7 is formed by arranging a treatment table 1, a cabinet 2 and a chest 3 on the desired floor in such a manner that they extend over the floor and the wall or walls. Namely, in the case of orthodontic treatment, the treatment table 1 makes it necessary for the patient to take a supine posture to receive treatment, and accordingly a horizontal treatment table is used and installed fixedly on the floor 6 laid down in advance. A worktable 27 of the cabinet 2 has a substantially triangle shape with a right-angle at the wall side and the cabinet 2 illustrated is of a standard type, and the size of the cabinet 2, for example in a preferred embodiment, is designed to be 90 cm in height up to the worktable 27, 125 cm in the length of one side 2a forming the height of a right-angled triangle and 100 cm in the length of the other side 2b forming the base side of the triangle. The cabinet 2 is provided on the upper surface thereof with a sink 21, a disinfectant solution tub 22, dust chute 23 and a paper towel case 24 so as to facilitate sanitary control such as hand washing and also to permit on the cabinet 2 the kneading or the like of an impression material necessary for a mouth (or tooth) model. Furthermore, an impression collecting material necessary for working out the mouth model is placed and stored in a chest 26 having an openable lid 25 mounted on the top thereof. In addition thereto, the remaining space of the upper surface of the cabinet 2 is formed as a worktable 27 on which an electric welder 28 is installed so as to be freely drawn out. The cabinet 2 is provided on the body thereof with stepwise drawers 29 which are adapted to store instruments by groups in the order of frequency in use such as standard sets (pincers, mirror, vacuum tip, etc.,) bands, brackets, etc., and materials necessary for orthodontics. This cabinet 2 is arranged transversely diagonally to the left of the head portion of the table 1 installed on the floor 6 and is installed on the floor in the manner that the surface of one side 2a forming the height of the right-angled triangular prism makes contact with the wall surface W and the surface of the other one side 2b forming the base side makes a right angle with the wall surface W. The chest 3, as shown in FIG. 4, is provided on the upper and lower parts thereof with several steps of shelves 31 for orderly placing mouth models thereon and also provided vertically in the middle with a drawer 32 for storing rubber rings therein, and further provided with a drawer (not shown) for storing materials for adjusting the bands of chin caps therein, a rack 34 for storing various charts such as analysis data, measurement recording paper, tissue paper, paper towel, etc., therein, and a drawer 35 for storing measuring instruments therein. And this chest 3 includes a panel 36 extending from one side edge of the chest 3 at right angles to the front side of the chest 3, and this panel 36 is mounted inside with a mirror 37 which the patient himself uses for practice. And the chest 3 is provided in series to one side 2b of the cabinet 2 and forms a partition A having an inverted L-shape in plane between the areas 8 and 7 by means of the cabinet 2, chest 3 and panel 36. The numeral 4 designates a panel on the lower end of which is provided on sofa 9 so that the patient together with his parent can sit thereon. Furthermore, devices for measuring the height and weight of the patient are disposed by the side of the sofa 9, and one of such devices is shown in FIG. 4 as a step 10 for measuring height. The panel 4 constitutes a partition board B L-shaped in plane in an opposed relation to the inverted L-shaped partition A formed by the cabinet 2 and chest 3, and bears at one side edge against the wall W at right angles therewith. A space C is formed both by the panel 4 functioning as this partition board B and by the partition A. The numeral 5 designates a desk which is disposed in substantially the middle of the space C and which is placed on the floor with one end thereof bearing against the wall W. The desk 5 is provided on the top surface with an X-ray film viewer 51. The space extending between the partitions A and B and having the desk 5 disposed therein provides the consultation area 8.

In FIG. 4, the numeral 101 designates a book shelf; 102 and 102 designate elongated pockets formed respectively on the tops of the chest 3 and cabinet 2, and these pockets are used for arranging jardinieres or the like thereon for ornamental purposes.

A description will now be given of one order of procedure in which the operator carries out orthodontic treatment by use of the orthodontic unit disposition structure according to the invention. When a child patient comes with his parent to a doctor's office, first, (1) the operator sits face to face wtih the patient and his parent in the consultation area with the desk between the former and the latter, and the operator makes an examination of the main condition and case history of the patient through an exchange of questions and answers and then carefully observes his face shape, the oral cavity, especially the state of occlusion and records the results obtained. Also, he measures the body of the patient by use of the instruments for measuring height, weight, etc., provided in the consultation area 8. This body measurement is necessary for the analysis of growth. (2) The operator takes a model-impression of the patient on the treatment table by use of the mouth model material stored in the chest 26 of the cabinet in the consultation area 8. The gypsum chin model prepared out of the collected original model in the workshop or the like is stored on the classification shelf 31 of the chest 3 in the clinical area 7. The character m in FIG. 4 designates the chin model. (3) A preliminary examination of face photograph, panoramic X-ray photograph, etc., is taken in the other places (other than the orthodontic unit disposition structure of the invention) and such photographs are stored in the rack 34 of the chest 3. (4) When the collection of data described in the above first to fourth items is over, the operator analyzes the case on the basis of the data. Because the desk 5 in the consultation area 8 is provided on the top thereof with an X-ray film viewer 51 and because the measuring instruments are stored in the drawer 35 of the chest 3, speedy and accurate data analysis can be made in the consultation area 8. (5) The operator makes a close treatment program on the basis of the data analysis and gives a detailed explanation to the patient and his parent in the consultation area 8. (6) The operator enters into treatment operation on the basis of the treatment program, and makes treatment in the clinical area 7 disposed in an adjacent relation with the consultation area 8. Namely, an orthodontic device is mounted in the mouth by carrying, for example, the device mounting work in the order of (7) separation between the teeth, (8) adaptation of the band to the teeth, (9) attachment of the band to the teeth, (10) insertion of an arch wire, (11) ligation of a ligature, and (12) mounting of a rubber ring. Because the cabinet is disposed tranversely diagonally to the headrest 11 of the treatment table 1 and because various instruments necessary for orthodontic treatment are stored in the cabinet 2 in the order of frequency in use, the operator can carry out the device mounting work very smoothly. (13) Thereafter, the operator or his assistant teaches the patient how to attach and detach the rubber ring and to adjust the chin cap before the mirror 37 disposed for patient's practice purposes in the consultation area 8.

As can be understood from the items 1–13 described above, the operator finishes an initial examination, first treatment and training, and instruction, and thereafter at suitable intervals of days the operator continues to observe the condition of the patient and detaches the orthodontic device, takes his mouth model, and continuously makes growth analysis. And every time the operator acts in that way, he makes adjustment of the ligature to thereby continuously carry out orthodontic treatment.

As is understood from the description given so far, the invention has rendered it possible to rationalize the treatment work of the operator and his assistant around a patient in the treatment area and to make an examination of the patient with his parent in attendance through an exchange of questions and answers, diagnosis, and instruction systematically, because the clinical area 7 and consultation area 8 are provided in an adjacent relation with each other by arranging the cabinet 2 transversely diagonally to the head of the horizontal treatment table with the table 1 placed as the center and partitioning the unit disposition structure into the treatment area 7 and the consultation area 8 both by means of the chest 3 provided in series to one side 2b of the cabinet and by means of the panel 4 (partition B) provided in an opposed relation with the cabinet and the chest 3. In this manner, the invention makes it possible for the operator to carry out rational treatment for exclusive use in orthodontics and is also effective for placing the treatment room itself in order.

Having described our invention as related to the preferred embodiment shown in the accompanying drawings, it is our intention that the invention be not limited by any of the details of the description, unless otherwise specified, but rather be construed broadly within the spirit and scope as set out in the accompanying claims.

We claim:

1. An orthodontic unit disposition structure, designed to be capable of carrying out an initial diagnosis and treatment and training of a patient in a clinical area and a consultation area, comprising:
   a horizontal treatment table;
   a cabinet substantially right-angled triangular in plane and arranged transversely diagonally to the head of said table and adapted to store orthodontic instruments and materials and having a worktable and sanitary parts provided on the top thereof;
   a chest disposed in series with said cabinet and disposed transversely diagonally to the head of said treatment table;
   a panel disposed substantially parallel with and spaced in an opposed relation from said chest and said cabinet; and
   a desk disposed in substantially parallel space provided by said panel, said cabinet, and said chest, whereby treatment table, cabinet, chest, panel, and desk are installed on the floor and the floor having said treatment table placed thereon is used as the clinical area and the floor having said desk placed thereon is used as the consultation area.

2. An orthodontic unit disposition structure according to claim 1 wherein a sofa for patient and his or her parent is installed in said consultation area.

* * * * *